US007378233B2

(12) United States Patent
Sidransky et al.

(10) Patent No.: US 7,378,233 B2
(45) Date of Patent: May 27, 2008

(54) BRAF MUTATION T1796A IN THYROID CANCERS

(75) Inventors: David Sidransky, Baltimore, MD (US); Yoram Cohen, Baltimore, MD (US); Mingzhao Xing, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 145 days.

(21) Appl. No.: 10/821,203

(22) Filed: Apr. 9, 2004

(65) Prior Publication Data
US 2005/0048533 A1 Mar. 3, 2005

Related U.S. Application Data

(60) Provisional application No. 60/462,046, filed on Apr. 14, 2003.

(51) Int. Cl.
*C12Q 1/00* (2006.01)
*C12P 19/34* (2006.01)
*G01N 33/50* (2006.01)

(52) U.S. Cl. .............................. 435/4; 435/91.2; 436/64
(58) Field of Classification Search ...................... None
See application file for complete search history.

(56) References Cited

FOREIGN PATENT DOCUMENTS

WO WO95/19448 * 7/1995
WO WO03/008583 * 1/2003

OTHER PUBLICATIONS

Davies et al. (2002, Nature 417:949-954.*
Wolf et al. (2002, Hautarzt. 53(5):332-2) (abstract only).*
Tockman et al (Cancer Res., 1992, 52:2711s-2718s).*
Kimura et al. (Apr. 1, 2003, Cancer Research 63:1454-1457).*
Tyler et al. (1994, Surgery 116(6):1054-60) (abstract only).*
Shaag et al (BBRC, 1997, vol. 233, pp. 637-639).*
New England Biolabs On-line Catalog (1998-1999), listing for TspR1.*
Weber et al., "Active Ras Induces Heterodimerization of cRraf and BRaf[1]", *Cancer Research*, May 1, 2001, pp. 3595-3598, vol. 61.
Hogrefe R., "An Antisense Oligonucleotide Primer", *Antisense and Nucleic Acid Drug Development*, 1999, Table 1 updated 2002, pp. 351-357, vol. 9.
Wilhelm et al., "Bay 43-9006: Preclinical Data", *Current Pharmaceutical Design*, 2002, pp. 2255-2257, vol. 8.
Cohen et al., "BRAF Mutation in Papillary Thyroid Carcinoma", *Journal of the National Cancer Institute*, Apr. 16, 2003, pp. 625-627, vol. 95, No. 8.
Namba et al., "Clinical Implication of Hot Spot BRAF Mutation, V599E, in Papillary Thyroid Cancers", *The Journal of Clinical Endocrinology & Metabolism*, 2003, pp. 4393-4397, vol. 88(9).
Huang et al., "Gene Expression in Papillary Thyroid Carcinoma Reveals Highly Consistent Profiles", *Proceedings of the National Academy of Sciences*, Dec. 18, 2001, pp. 15044-15049, vol. 98, No. 26.

Kimura et al., "High Prevalence of BRAF Mutations in Thyroid Cancer: Genetic Evidence for Constitutive Activation of the RET/PTC-RAS-BRAF Signaling Pathway in Papillary Thyroid Carcinoma[1]", *Cancer Research*, Apr. 1, 2003, pp. 1454-1457, vol. 63.
Daum et al., "The Ins and Outs of Raf Kinases", *Elsevier Science Ltd.*, Nov. 1994, pp. 474-480.
Davies et al., "Mutations of the BRAF Gene in Human Cancer", *Nature*, Jun. 27, 2002, pp. 949-954, vol. 417.
Cripps et al., "Phase II Randomized Study of ISIS 3521 and ISIS 5132 in Patients with Locally Advanced or Metastatic Colorectal Cancer: A National Cancer Institute of Canada Clinical Trials Group Study[1]", *Clinical Cancer Research*, Jul. 2002, pp. 2188-2192, vol. 8.
Yin et al., "RNA-mediated Gene Regulation System: Now and the Future (Review)", *International Journal of Molecular Medicine*, 2002, pp. 355-365, vol. 10.
Collisson et al., "Treatment of Metastatic Melanoma with an Orally Available Inhibitor of the Ras-Raf-MAPK Cascade[1,2]" *Cancer Research*, Sep. 15, 2003, pp. 5669-5673, vol. 63.
Kolch et al., "Animation of the Organisation and Function of the Ras-Raf-MEK-ERK Pathway", Expert Reviews in Molecular Medicine: http://www.expertreviews.org, Accession Information: (02)00444- 1h.htm (shortcode: swf001 wkg); Aug. 14, 2002 (Abstract only).
Mullen et al., "Antisense Oligonucleotide Targeting of raf-1: Importance of Raf-1 mRNA Expression Levels and Raf-1-Dependent Signaling in Determining Growth Response in Ovarian Cancer", *Clinical Cancer Research*, Mar. 15, 2004, pp. 2100-2108, vol. 10(6). (Abstract only).
Lee et al., "BAY-43-9006 Bayer/Onyx", *Current Opinion of Investigative Drugs*, Jun. 2003, pp. 757-763, vol. 4(6). (Abstract only).
Wan et al., "Mechanism of Activation of the RAF-ERK Signaling Pathway by Oncogenic Mutations of B-RAF", *Cell*, Mar. 19, 2004, pp. 855-867, vol. 116(6). (Abstract only).
Bollag et al., "Raf Pathway Inhibitors in Oncology", *Current Opinion Investigative Drugs*, Dec. 2003, pp. 1436-1441, vol. 4(12). (Abstract only).

* cited by examiner

*Primary Examiner*—Karen A. Canella
(74) *Attorney, Agent, or Firm*—Banner & Witcoff, Ltd.

(57) ABSTRACT

The BRAF gene has been found to be activated by mutation in human cancers, predominantly in malignant melanoma. We tested 476 primary tumors, including 214 lung, 126 head and neck, 54 thyroid, 27 bladder, 38 cervical, and 17 prostate cancers, for the BRAF T1796A mutation by polymerase chain reaction (PCR)-restriction enzyme analysis of BRAF exon 15. In 24 (69%) of the 35 papillary thyroid carcinomas examined, we found a missense thymine (T)→adenine (A) transversion at nucleotide 1796 in the BRAF gene (T1796A). The T1796A mutation was detected in four lung cancers and in six head and neck cancers but not in bladder, cervical, or prostate cancers. Our data suggest that activating BRAF mutations may be an important event in the development of papillary thyroid cancer. Moreover, BRAF mutation reliably predicts a poor prognosis for papillary thyroid carcinomas.

15 Claims, 2 Drawing Sheets

BRAF MUTATION T1796A IN THYROID CANCERS

This application claims priority to provisional U.S. Application Ser. No. 60/462,046, filed Apr. 14, 2003.

FIELD OF THE INVENTION

The invention relates to diagnostic, therapeutic, and prognostic methods for thyroid cancers.

BACKGROUND OF THE INVENTION

Raf kinase is a key component of the RAS→Raf→MEK→ERK/MAP kinase signaling pathway, which plays a fundamental role in the regulation of cell growth, division and proliferation, and, when constitutively activated, causes tumorigenesis (19). Among several isoforms of Raf kinase, the B-type, or BRAF, is the strongest activator of the downstream MAP kinase signaling (25). The BRAF gene is located on Chromosome 7.

The RAF proteins are highly conserved serine/threonine protein kinases that have an important role in cell proliferation, differentiation, and programmed cell death (1). The RAF proteins activate mitogen-activated protein kinase kinase (MEK), which in turn activates the mitogen-activated protein kinase (MAPK) pathway (2). Inappropriate and/or continuous activation of this pathway provides a potent promitogenic force resulting in abnormal proliferation and differentiation in many human cancers (3). Davies et al. (4) reported that BRAF is frequently mutated in a variety of human tumors, especially in malignant melanoma and colon carcinoma. The most common reported mutation was a missense thymine (T)→adenine (A) transversion at nucleotide 1796 (T1796A; amino acid change in the BRAF protein is $Val^{599}$→$Glu^{599}$) observed in 80% of the malignant melanoma tumors. Functional analysis revealed that this transversion was the only detected mutation that caused constitutive activation of BRAF kinase activity, independent of RAS activation, by converting BRAF into a dominant transforming protein (4).

Papillary thyroid cancer (PTC) is the most common thyroid cancer, accounting for about 80% of thyroid malignancies (20). Although PTC is usually indolent and curable with surgical thyroidectomy followed by radioiodine treatment, many patients do have recurrence and some become incurable and die (18); (15); (17); (24). Consequently, it is important to undertake appropriate risk stratification and prognostic evaluation for patients with PTC in order to provide optimal clinical management of the cancer. This is usually achieved based on evaluation of various clinicopathologic risk factors, such as the age and gender of the patient, the size of the tumor, and extrathyroidal invasion and metastasis status (18); (15); (17); (24). With the demonstration of the oncogenic effect of the BRAF T1796A transversion mutation (4), it is conceivable that BRAF mutation plays an important tumorigenic role in PTC and may thus affect the clinicopathologic outcomes of these cancers. Indeed, it has recently been shown that BRAF mutation was associated with a higher prevalence of extrathyroidal invasion and advanced pathologic stage of PTC (27). In another recent analysis on PTC, however, no significant association of the BRAF mutation with extrathyroidal invasion was demonstrated although a marginally significant association of the BRAF mutation with advanced pathologic stage was observed (26). There is a need in the art for improved and/or additional means for detecting, diagnosing, categorizing, treating, and predicting outcomes for thyroid cancers.

BRIEF SUMMARY OF THE INVENTION

In a first embodiment of the invention a method is provided for distinguishing malignant from benign thyroid samples. The presence of a T→A transversion at nucleotide 1796 of BRAF according to SEQ ID NO: 1 is determined in a thyroid sample of a human. The presence of the transversion indicates a malignant thyroid neoplasm and absence of the transversion indicates a benign neoplasm or sample.

In a second embodiment a method for distinguishing malignant from benign thyroid samples is provided. The presence of a T→A transversion at nucleotide 1796 of BRAF according to SEQ ID NO: 1 is determined in a blood sample of a human. The presence of the transversion indicates a malignant thyroid neoplasm in the human and absence of the transversion indicates a benign neoplasm or no neoplasm.

In a third embodiment of the invention a method is provided for detecting a mutation at nucleotide 1796 of BRAF. All or part of exon 15 of BRAF from a test sample is amplified to form amplified products. The part of exon 15 comprises at least nucleotides 1792 to 1799 of BRAF. The amplified products are digested with restriction endonuclease TspRI to form digested products. A mutation at nucleotide 1796 is identified if the digested products contain one fragment fewer than digested products formed when using wild-type BRAF as a template for amplifying and digesting; or one additional fragment compared to digested products formed when using wild-type BRAF as a template for amplifying or digesting.

In a fourth embodiment of the invention a method is provided for treating a thyroid cancer patient. An effective amount of an inhibitor of BRAF serine/threonine kinase is administered to the patient.

In a fifth embodiment of the invention a method is provided for treating a thyroid cancer patient. An effective amount of an inhibitor of the Ras-Raf-MAPK pathway or the Raf/MEK/ERK signaling pathway is administered to the patient.

These and other embodiments of the invention provide the art with additional methods to successfully manage thyroid cancers.

BRIEF DESCRIPTION OF THE DRAWINGS

FIG. 1. TspRI restriction enzyme analysis (FIG. 1A) and exon 15 sequence analysis (FIG. 1B) of BRAF.

DETAILED DESCRIPTION OF THE INVENTION

Figure 1A:
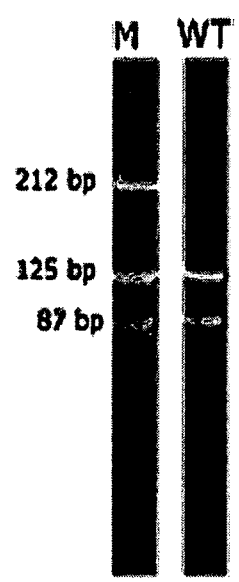
FIG. 1A) Restriction pattern of the T1796A mutation. Lane M=mutant T299; lane WT=wild-type T486.

It is a discovery of the present inventors that T1796A mutations of the BRAF gene are common in thyroid carcinomas and that they can be used to distinguish between benign and malignant carcinomas. Moreover, the presence of the mutation bodes ill for a patient's survival and for the recurrence of the cancer.

The transversion mutation T1796A of the BRAF gene is known in the art. Any method of detecting the mutation may be used. These include, but are not limited to, amplifying and sequencing the region of the gene containing nucleotide 1796, amplifying and digesting with a restriction endonuclease whose recognition or cleavage site is destroyed by the mutation (such as TspRI), primer extension methods, and hybridization to allele specific oligonucleotides. Any method known in the art for detecting point mutations can be used. Genomic DNA, mRNA, or protein of the BRAF gene may be assayed to determine the transversion mutation.

A variety of samples from the patient can be tested for the transversion mutation. These include tissue samples, cytological samples such as fine needle aspirates, and blood. Blood samples include inter alia whole blood, serum, and plasma. Sputum, saliva, lymph, tears can also be tested. If a tissue sample is used it can have a follicular, a papillary, an indeterminate, or an undetermined morphology.

Determination of the presence or absence of the transversion in a sample can be used to provide a diagnosis, to decide whether to perform surgery, and to decide what drugs and or radiation will be used. Drugs which may be prescribed include chemotherapeutic agents, therapeutic antibodies, therapeutic anti-sense oligonucleotides or constructs, small interference RNAs, etc. A prognosis may constitute an estimated life expectancy, a prediction of recurrence, or a recommendation for an aggressive or non-aggressive therapeutic regimen. A prognosis may also include a recommendation of a schedule for monitoring for recurrence or metastasis.

When using a restriction endonuclease assay to detect a transversion at nucleotide 1796, one typically amplifies a fragment of the BRAF gene which comprises this nucleotide. The fragment will typically have a sufficient number of nucleotides on either side of the transversion such that a change in size of a fragment containing the transversion will be readily detectable. Moreover, a sufficient number of nucleotides will be present such that the full recognition and/or cleavage site is present in the fragment. For example, when using the enzyme TspRI in an assay, at least nucleotides 1792 to 1799 will typically be present in the fragment. If a restriction enzyme cleavage and/or recognition site is destroyed by a transversion mutation, then two fragments of a wild-type allele will be joined. Thus from the mutant allele, there will be one fewer fragments. If both alleles in the sample are mutant, then there will be one fewer fragment in the sample. If only one allele is mutant and one allele remains wild-type, then the sample will have an additional fragment (the fused fragments) relative to a wild-type sample.

Thyroid cancers can be treated using any agent which will inhibit BRAF expression or activity or an inhibitor of the Ras-Raf-MAPK or Raf/MEK/ERK pathways. Typically the presence of a BRAF transversion mutation will be detected prior to treatment. Suitable inhibitors include antibodies that bind to BRAF kinase or other components of the pathway. The antibodies can, but need not, bind preferentially to BRAF relative to other isoforms of RAF kinase. Antisense oligonucleotides can be administered. The antisense oligonucleotides typically will have modified chemical structures to enhance stability in the body. One such modified structure contains phosphorothioates in the phosphate backbone. Other modifications which reduce nuclease degradation and retain susceptibility to RNase H can also be used. For example, 2'-O-methyl nucleosides can be used, particularly on the 5' and 3' ends. The oligonucleotides can be complementary to BRAF mRNA or to other mRNA encoding components of the pathway. Some such oligonucleotides which can be used are ISIS 5132 and ISIS 13650. Oligonucleotides can be complementary to various portions of the mRNA. The region surrounding the start codon may be targeted, as can splice sites. Double stranded inhibitory RNA molecules can also be used. These are typically about 20-26 bases in length or preferably 20-23 bases in length. The molecules preferably contain 2-nucleotide 3' overhangs. They can be complementary to BRAF mRNA or to mRNA encoding other components of the pathway. Small molecule inhibitors of the kinase activity of BRAF or the pathways can also be used. Such inhibitors include CI 1040 and BAY 43-9006.

Papillary and follicular thyroid carcinomas originate from thyroid follicular epithelial cells. To date, oncogenic mutations in RAS and RET/PTC rearrangements have been observed in follicular thyroid carcinoma and papillary thyroid carcinomas, respectively (5,6). RAS mutations are common in follicular thyroid cancers, reaching 50% in some studies, but are less common (5%-20%) in papillary thyroid tumors (5). Our observation of a high frequency of BRAF-activating mutations in papillary thyroid carcinoma suggests that BRAF activation and, in turn, activation of the RAF/MEK/MAPK signaling pathway, is a common biologic mechanism in the development of human papillary thyroid carcinoma. This observation is also consistent with the reported inverse association between the presence of BRAF and RAS mutations in other cancer types (4,7,8). The relationship between BRAF T1796A mutation and RET/PTC rearrangements remains to be explored.

The importance of the RAS pathway in thyroid cancers is further suggested by the common presence of RET mutations in medullary thyroid tumors and their transforming effect through activation of the RAS/RAF/MEK pathway (9). Moreover, activation of the RAS/RAF/MEK/MAPK pathway is known to induce genomic instability in thyroid PCCL-3 cells (10), and inhibition of the MAPK pathway has led to decreased cellular proliferation of human thyroid cancer cell lines (11). Thus, activation at various points in the RAS/RAF/MEK/MAPK pathway is a key event in the most common type of malignant thyroid tumor. The high frequency of BRAF mutations in melanoma and papillary thyroid carcinoma suggests that inhibition of BRAF activity by the newly developed RAF kinase inhibitors (12) may offer a new strategy in the treatment of these tumors. Our results have identified the BRAF T1796A mutation and the activation of the RAF/MEK/MAPK signaling pathway as a major mechanism in the development of primary papillary thyroid carcinoma.

PTC is the most common thyroid cancer, accounting for the vast majority of thyroid malignancies. Although PTC is generally an indolent cancer and, with the current standard treatments, has an excellent long-term survival rate (18,15, 17,24), many patients have recurrence and some become incurable and die. To reduce the morbidity and mortality further and improve the efficiency of the current management for PTC patients, it is important to conduct a proper risk stratification and prognostic evaluation in order to optimize the management for these patients. This is traditionally achieved based on clinicopathologic factors of the tumor and the patient that may affect the disease outcome. Large tumor size, extrathyroidal invasion, distant metastasis, advanced pathological stage of the tumor, multifocality, older age of the patient at time of diagnosis, and male gender are all to some extent associated with a poorer prognosis (18,15,17,24). Neck lymph node metastasis, particularly when with extracapsular invasion, was shown to predict tumor recurrence (33). In general, though, the prognostic significance of lymph node metastasis in PTC patients may be related to the age of patient at diagnosis (17). In young patients, neck lymph node involvement may not impose significant risk for tumor progression and recurrence, particularly if the patient has properly received post-operative radioiodine ablation therapy. In older patients, however, lymph node involvement is associated with increased risk of cancer progression and recurrence. Among all these risk factors, extrathyroidal invasion is one of the most reliable prognostic factors that predict a high probability of cancer progression and recurrence. Some of the other factors, however, do not seem to be consistently good prognostic factors in all studies. An effective and reliable prognostic factor, such as a mutation biomarker, could improve further the current risk and prognostic evaluation of PTC clinically.

The T1796A transversion BRAF mutation is the most common known genetic alteration in thyroid cancer and exclusively occurs in PTC (23,13,28,32,16,26,27,29). As this mutation was demonstrated to be oncogenic (4), we proposed that it played a significant role in thyroid tumorigenesis and in determining the phenotypic behaviors of PTC and therefore might be a useful biomarker that can be added to the panel of the prognostic factors discussed above for the risk evaluation of PTC patients. We therefore have examined the BRAF T1796A transversion mutation in PTC from a large group of patients and analyzed the correlation of this mutation with those clinicopathologic parameters that are known to predict a poor prognosis of PTC. We found a significant association of this mutation with tumor extrathyroidal invasion, advanced pathologic stages, and neck lymph node metastasis, and, not surprisingly, also with a higher incidence of cancer recurrence during the clinical follow-up after thyroidectomy (Table 2). This association still existed even after a multivariate analysis with an adjustment for the potential confounding factors including patient age and gender, tumor size and multifocality, and radioactive I-131 treatments (Table 4). Kaplan-Meier estimate of the effect of BRAF mutation on tumor recurrence clearly showed a poorer tumor recurrence-free probability for BRAF mutation-positive PTC patients (FIG. 2), and, even after adjustment for the above-mentioned confounding variables, the relative risk for tumor recurrence associated with BRAF mutation was statistically significant. Moreover, when different subtypes of PTC were analyzed, we found that BRAF mutation occurred more frequently in those subtypes of PTC (classic and tall cell variant) that were associated more often with extrathyroidal invasion, lymph node metastasis, and cancer recurrence (Table 3). Our study therefore suggests that BRAF mutation plays a significant role in determining the phenotypic behaviors of PTC and is a genetic indicator of poor prognosis for this type of thyroid cancer.

In a recent study on a series of PTC that was comprised mostly of American patients, a significant association of BRAF mutation with extrathyroidal invasion and advanced stages of the tumor was observed (27). In this study, unlike in the present one, no multivariate analysis on each of these pathologic parameters for an adjustment of potential confounding factors was performed. Clinical follow-up data on the patients were also not reported and therefore how BRAF mutation affected the cancer recurrence—an ultimate clinical outcome of the patients—was not clear. In addition, although a higher prevalence of lymph node metastasis was apparently associated with BRAF mutation in this study, it did not reach statistical significance, perhaps due to the need for a even larger number of PTC samples. Interestingly, this previous study showed a significant association of BRAF mutation with older age of the patients while ours failed to show so. A recent study on a large Japanese series of PTC with a similar number of cases to ours only showed a marginally significant association of BRAF mutation with advanced tumor stage, but no significant association of BRAF mutation with extrathyroidal invasion and lymph node metastasis was observed (26). However, BRAF mutation was associated with a higher incidence of distant metastasis in this study, although this large Japanese series has reported the lowest prevalence of BRAF mutation (29%) in PTC among the studies that have been reported so far. It is not clear if the role of BRAF mutation varies in PTC of patients from different ethnic backgrounds. The relationship of BRAF mutation with other known risk/prognostic factors apparently remains to be clarified in larger studies.

In summary, our work with careful statistical analysis has expanded the previous studies and demonstrated that BRAF mutation is associated with a number of pathologic features of PTC that are known to be predictors for a poor prognosis. We further showed that BRAF mutation was associated with a higher incidence of tumor recurrence, demonstrating the usefulness of BRAF mutation as a novel prognostic genetic marker in the risk and prognostic evaluation of patients with PTC. We suggest that it may be a useful strategy to examine the BRAF mutation status in the thyroid tumor of patients with PTC to identify those with BRAF mutation so they can be optimally managed. In this context, preoperative examination of BRAF mutation on fine needle aspiration specimens, which was recently demonstrated to be a reliable and sensitive method to detect BRAF mutation (30), could provide valuable guidance in planning for optimal thyroid surgery and subsequent vigilant clinical follow-up in patients with PTC.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

In this study, we investigated the frequency of BRAF T1796A mutation and further elucidated the importance of this mutation in various primary human tumors.

Figure 1B:
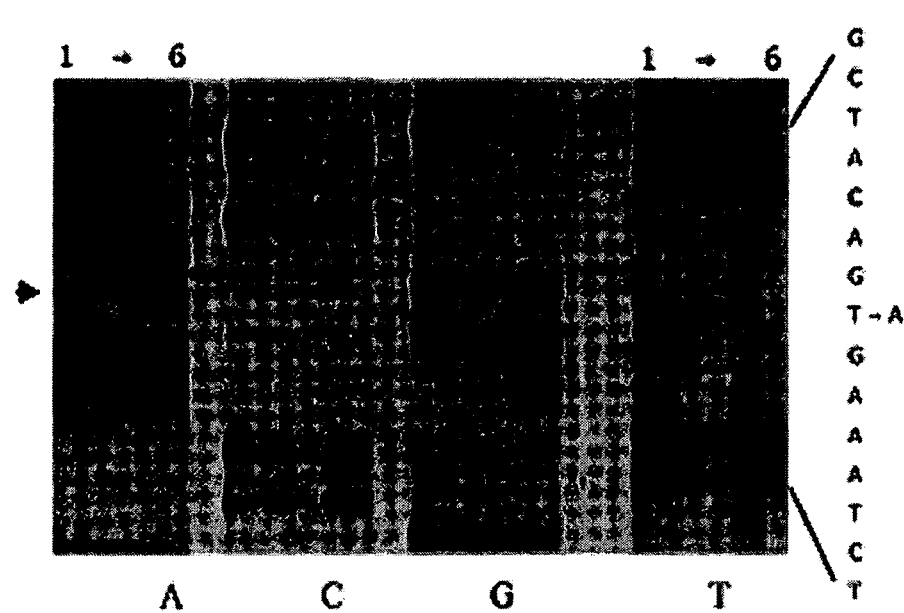
FIG. 1B) Manual DNA sequence gel of exon 15 from papillary thyroid samples harboring the T1796A mutation (arrowhead). Lane 1=T569; lane 2=T203; lane 3=a thyroid adenomatous hyperplasia (T530) negative for the T1796A mutation; lane 4=T228; lane 5=T171; and lane 6=melanoma cell line HTB72 that carries a homozygous T1796A mutation. The sequence is to the right.

We screened 476 primary tumors, including 214 lung, 126 head and neck, 54 thyroid, 27 bladder, 38 cervical, and 17 prostate cancers for the BRAF T1796A mutation by polymerase chain reaction (PCR)-restriction enzyme analysis. The samples were obtained from patients treated at The Johns Hopkins Medical Institutions (Baltimore, Md.) and were collected in our tissue bank. Written informed consent was obtained from each patient in accordance with the institutional review board at The Johns Hopkins Medical Institutions. PCR amplification of exon 15 followed by digestion of the exon 15 products by the restriction endonuclease TspRI identified the BRAF T1796A mutation. TspRI digestion of the PCR fragment yielded three major bands at 125 base pairs (bp), 87 bp, and 12 bp in the wild-type allele. The T1796A mutation abolished the restriction site, resulting in a prominent 212-bp band from the mutant allele and residual bands from the normal allele (FIG. 1, A⇓). Reamplification of BRAF exon 15 followed by direct manual sequencing of five samples validated the results of the TspRI assay (FIG. 1, B⇓). As positive controls for the BRAF T1796A mutation, we used melanoma cell lines HTB71, HTB72, and A2058; for negative controls, we used cell lines ME180 (cervical cancer) and HCT116 (colorectal carcinoma).

The BRAF T1796A mutation was identified in 24 (69%) of 35 papillary thyroid carcinomas (Table 1⇓), six (4.8%) of 126 head and neck cancers, and four (1.9%) of 214 lung cancers. Moreover, we analyzed nine common thyroid cell lines (KAK1, KAT5, KAT7, KAT10, DRO, ARO, MRO 87-1, WRO-821, and C643) and found the same BRAF mutation in six (67%) of the nine lines. We also completely sequenced exons 11 and 15 in all T1796A-negative papillary thyroid cancers and in 10 T1796A-positive tumors but did not identify additional BRAF mutations. We did not identify any mutations in bladder, cervical, and prostate primary tumors, and no mutation was identified in biopsy samples from 20 patients with benign thyroid conditions (nodular goiter, follicular adenoma, atypical follicular adenoma, and adenomatous hyperplasia), 13 patients with follicular thyroid carcinoma, three patients with medullary thyroid carcinoma, and three patients with Hürthle cell carcinoma.

Example 2

In the present study on a large series of thyroid cancer patients, we investigated the correlation of BRAF mutation with various clinicopathologic characteristics of the tumor and, to take a further step, we also examined the effect of BRAF mutation on cancer recurrence over a long period of clinical follow-up. We found a significant association of BRAF mutation with extrathyroidal invasion and advanced pathologic stages of the tumor. In addition, we also observed a significantly higher association of BRAF mutation with neck lymph node metastasis and cancer recurrence, demonstrating that BRAF mutation is a novel prognostic biomarker that predicts a poor prognosis for PTC.

Patients and Clinicopathologic Data Collection

Based on a protocol approved by the Institutional Review Board of the Johns Hopkins University School of Medicine and with appropriate patient consent, we retrospectively reviewed the clinical records of 171 patients who had thyroidectomy for thyroid tumors over the last 10 years at the Johns Hopkins Medical Institutions (including Johns Hopkins Hospital and Johns Hopkins Bayview Medical Center) and whose thyroid tumor tissues were available for BRAF mutation analysis. Information on clinicopathologic characteristics of the tumor and clinical course of each patient (e.g., cancer recurrence and history of radioiodine treatment), as specified in the section of Results, was collected through this review. The histopathologic description, including the histological diagnosis and tumor subtype classification, was made by several experienced pathologists at the Johns Hopkins Medical Institutions based on standard criteria. The tumors studied included 123 PTC, 6 follicular thyroid cancers, 3 Hurthle cell thyroid cancers, 3 medullary thyroid cancers, and 36 benign thyroid neoplasms. Because BRAF mutation was found exclusively in PTC, only the PTC patients were analyzed for the correlation between the clinicopathologic characteristics and BRAF mutation status of the tumor. The demographic information of these patients is shown in Table 2 of the Results section. All the PTC patients received total or near total thyroidectomy. The clinical "follow-up" time for those patients who had cancer recurrence was defined as the time period from the initial thyroid surgery to the first tumor recurrence. For those patients who did not have cancer recurrence, the "follow-up" time was defined as the time from the initial thyroid surgery to the most recent clinical evaluation at the Johns Hopkins Medical Institutions. The follow-up durations for each group of patients are shown in Table 2.

Thyroid Tumor Tissues and DNA Isolation

Fresh frozen or paraffin-embedded PTC samples from patients were microdissected and DNA isolated as previously described (31). Briefly, after microdissection of the tissues, and after a 3-h treatment at 48° C. with xylene for tissues dissected from paraffin-embedded samples, the samples were subjected to digestion with 1% SDS and 0.5 mg/ml proteinase K at 48° C. for 48 h. To facilitate the digestion, a midinterval addition of a spiking aliquot of concentrated SDS-proteinase K was added to the sample tubes. DNA was then isolated from the digested tissues by standard phenol-chloroform extraction and ethanol precipitation procedures. In some cases, DNA isolated from fine needle biopsy specimens was used instead.

Detection of BRAF Mutation

The BRAF T1796A mutation was analyzed on all the tumor samples in the present study, using genomic DNA by direct sequencing and a colorimetric method using the Mutector Kit (TrimGen, Baltimore, Md.) following the manufacturer's instructions. For direct DNA sequencing, exon 15 of the BRAF gene was amplified using the primers previously described (4): TCATAATGCTTGCTCTGATAGGA (SEQ ID NO: 2; forward) and GGCCAAAAATTTAATCAGTGGA (SEQ ID NO: 3; reverse). The PCR was performed using a step-down protocol: 95° C. for 5 minutes×1 cycle; 95° C. for 1 minute, 60° C. for 1 minute, and 72° C. for 1 minute, ×2 cycles; 95° C. for 1 min, 58° C. for 1 minute, and 72° C. for 1 minute×2 cycles; 95° C. for 1 minute, 56° C. for 1 minute, and 72° C. for 1 minute×40 cycles; with a final extension at 72° C. for 5 minutes. The PCR products were subsequently subjected to Big Dye terminator Cycle Sequencing reaction and the sequence was read on an ABI PRISM 3100 Genetic Analyser (Applied Biosystems) and the T1796A mutation was identified on the nucleotide sequence.

The colorimetric method for BRAF mutation was based on the technique of shifted termination assay, which was demonstrated to have a 100% sensitivity and specificity for the detection of BRAF mutation (30). Briefly, in this assay, a specifically designed detection primer hybridizes to the target sequence of the BRAF gene with its 3' terminus ending just before the target base. The primer extends through the target base only if it is a T1796A transversion mutation. The extension ends at a termination base and multiple labeled nucleotides are incorporated through this process. The procedure was started with PCR amplification of exon 15 of the BRAF gene as described above, followed by hybridization of the PCR products to the specific primers attached to the strips. Primer extension was achieved through a PCR reaction. Color development was performed through an enzymatic reaction and the intensity of the color was measured at a wave length of 405 nm. The details were as described recently (30).

Statistical Analysis

Categorical data were summarized using frequencies and percents. Distributions of the continuous variables were assessed, and all but age at diagnosis were found to not be normally distributed. Therefore, these data were summarized with medians and interquartile ranges. Group comparisons of categorical variables were performed using the chi-square test or, for small cell sizes, Fisher's exact test. Non-parametric statistics were used to compare the continuous variables. Comparisons of two groups were evaluated with the Wilcoxon rank sum test and comparisons of three groups were done using the Kruskal-Wallis test. Multivariate logistic regression analyses were performed to assess the effect of BRAF mutation on clinicopathologic outcomes of tumor stage, neck lymph node metastasis, extrathyroidal invasion, and recurrence of the tumor, adjusting for age at diagnosis, gender, multifocality and tumor size. The analysis of the effect of BRAF mutation on tumor recurrence was also adjusted for I-131 treatment. Product-limit survival analysis (22) and the log-rank test (21) were used to evaluate the effect of BRAF mutation on cancer recurrence. Proportional hazards regression analysis on tumor recurrence (14) with adjustment for the same variables as the dichotomous outcome, was performed to examine the risk for cancer recurrence associated with BRAF mutation. Confidence intervals (CI) were computed by standard methods. All reported p values are two-sided. Analysis was performed using SAS Version 8.0 software (SAS Institute, Cary, N.C.).

Results

Confirmation of the T1796A BRAF Mutation in PTC

Since the T1796A transversion mutation is the most common BRAF mutation in human cancers (4) and is the only BRAF mutation found in thyroid cancer (specifically, PTC) with a high prevalence in all the studies reported so far (23); (13); (28); (32); (16); (26); (27); (29), we analyzed this particular mutation in thyroid tumors in the present study using both direct DNA sequencing technique and the calorimetric assay. As summarized in Table 1, consistent with previous reports, we found BRAF mutation only in PTC, but not in the follicular thyroid cancers, Hurthle cell thyroid cancers, medullary thyroid cancers, and benign thyroid neoplasms.

TABLE 1

Prevalence of BRAF Mutation in Various Thyroid Tumors

|  | BRAF Mutation/Total | % |
| --- | --- | --- |
| Papillary (overall) | 54/123 | 44 |
| Classic Papillary | 40/69 | 58 |
| Follicular Variant | 4/44 | 9 |
| Tall Cell Variant | 10/10 | 100 |
| Follicular Cancer | 0/6 | 0 |
| Hurthle Cell Cancer | 0/3 | 0 |
| Medullary Cancer | 0/3 | 0 |
| Benign Neoplasms | 0/36 | 0 |

Association of BRAF Mutation with High-Risk Pathologic Features of the PTC and a Higher Incidence of Cancer Recurrence We performed a clinicopathologic correlation analysis on BRAF mutation in the PTC patients. As shown in Table 2, the overall analysis of the 123 PTC patients revealed a significant association of BRAF mutation with extrathyroidal invasion, neck lymph node metastasis, and more advanced pathologic stages of the tumor at the initial thyroid operation. These three pathologic features are traditionally thought to be associated with a high risk for poor prognosis of thyroid cancer. BRAF mutation was also associated with a significantly higher incidence of cancer recurrence after thyroidectomy. Except for two cases of distant metastasis with persistent disease, all the recurrences were local in the neck. There was no significant association of BRAF mutation with a particular gender or age of the patient and the size or multifocality of the tumor. There was also no significant difference in postoperative radioiodine-131 treatment in terms of the number and doses between the BRAF mutation-positive and negative groups.

TABLE 2

Correlation between clinicopathologic characteristics and BRAF mutation status in patients with papillary thyroid cancer. Median (interquartile range) or N (%).

|  | BRAF+ | BRAF− | P value |
| --- | --- | --- | --- |
| N (total) | 54 | 69 |  |
| Age at diagnosis | 45.5 (35-58) | 46.0 (37-56) | 0.89 |
| Gender, male | 16 (30%) | 22 (32%) | 0.79 |
| Tumor Size, cm | 2.0 (1.3-3.0)* | 2.4 (1.5-3.5)** | 0.13 |
| Extrathyroidal invasion | 22 (41%) | 7 (10%) | <.0001 |
| Lymph node metastasis | 28 (55%)*** | 14 (20%) | <.0001 |
| Tumor stage |  |  | 0.049 |
| I | 17 (35%) | 22 (32%) |  |
| II | 16 (33%) | 37 (54%) |  |
| III | 14 (29%) | 8 (12%) |  |
| IV | 2 (4%) | 2 (3%) |  |
| Tumor Stage, III/IV | 16 (33%)+ | 10 (14%) | 0.019 |
| Tumor recurrence | 9 (17%) | 3 (4%) | 0.022 |
| Multifocality | 22 (41%) | 23 (33%) | 0.40 |
| Number of I-131 treatments | 1 (1-1) | 1 (1-1) | 0.083 |
| Total I-131 dose | 100.4 (76.2-105.4) | 100.0 (30-103) | 0.15 |
| Dose/Treatment | 100.0 (77.0-105.0) | 100.0 (100.0-104.5) | 0.82 |
| Total follow-up (months) | 10.5 (1-27) | 14.0 (2-27) | 0.82 |

*Eight cases had no information on tumor size;
**Three cases had no information on tumor size;
***Three cases had no information on the status of lymph node metastasis. If, on a conservative assumption, all these three cases had no lymph node metastasis and were included in the analysis, the prevalence of lymph node metastasis in BRAF mutation-positive group would be 52% (instead of 55%) and the p value would be 0.0003 (instead of <0.0001).
+Five cases had no sufficient data to define tumor stage in the BRAF mutation-positive group. If, on a conservative assumption, all these five cases had a tumor stage less than III/IV and were included in the analysis, the prevalence of tumor stages III/IV in BRAF mutation-positive group would be 30% (instead of 33%) and the p value would be 0.041 (instead of 0.019).

As shown in Table 1, in the present series of PTC, BRAF mutation occurred most frequently in classic PTC (58%) and tall cell variant PTC (100%) and less frequently in follicular variant PTC (9%). This difference is statistically highly significant (Table 3). A significant difference in the high-risk pathologic features of extrathyroidal invasion and neck lymph node metastasis as well as cancer recurrence was also seen among these different subtypes of PTC, correspondingly with a higher occurrence in the classic and tall cell variant PTC and a much lower occurrence in the follicular variant PTC (Table 3). We did not find significant differences in the patient age and gender, tumor multifocality, and radioiodine treatments in these different tumor groups in the present study. The difference in tumor size among different tumor subtype groups was significant apparently due to the relatively large size of the tumors in the follicular variant group and small size in the classic PTC group examined in the present study.

TABLE 3

Comparison of the clinicopathologic characteristics and BRAF mutation status in various subtypes of papillary thyroid cancers. Median (interquartile range) or N (%).

| Characteristic | Classic | Follicular | Tall Cell | P value |
|---|---|---|---|---|
| N (total) | 69 | 44 | 10 | |
| BRAF+ Mutation | 40 (58%) | 4 (9%) | 10 (100%) | <.0001 |
| Age at diagnosis | 45.0 (38-57) | 46.5 (33-55) | 56.0 (40-76) | 0.18 |
| Gender, male | 25 (36%) | 11 (25%) | 2 (20%) | 0.33 |
| Tumor Size, cm | 1.8 (1.1-2.7)* | 2.9 (2.0-3.5)** | 2.5 (2.0-5.5) | 0.0013 |
| Extrathyroidal invasion | 21 (30%) | 1 (2%) | 7 (70%) | <.0001 |
| Lymph node metastasis | 30 (45%)*** | 5 (11%) | 7 (70%) | <.0001 |
| Tumor stage | | | | 0.11 |
| I | 24 (38%) | 13 (30%) | 2 (20%) | |
| II | 24 (38%) | 25 (57%) | 4 (40%) | |
| III | 15 (23%) | 4 (9%) | 3 (30%) | |
| IV | 1 (2%) | 2 (5%) | 1 (10%) | |
| Tumor stage, III/IV | 16 (25%)+ | 6 (14%) | 4 (40%) | 0.13 |
| Tumor recurrence | 9 (13%) | 0 (0%) | 3 (30%) | 0.0024 |
| Multifocality | 30 (43%) | 10 (23%) | 5 (50%) | 0.054 |
| Number of I-131 treatments | 1 (1-1) | 1 (1-1) | 1 (1-1) | 0.84 |
| Total I-131 dose | 100.0 (31.7-105.0) | 100.0 (51.4-103.4) | 105.0 (51.0-105.0) | 0.87 |
| Dose/Treatment | 100.0 (86.0-104.5) | 100.0 (100.0-104.5) | 105.0 (78.0-127.5) | 0.61 |
| Total follow-up (months) | 15.0 (2-27) | 12.5 (2-27) | 6.0 (1-20) | 0.58 |

*Ten cases had no information on tumor size;
**One cases had no information on tumor size;
***Three cases had no information on the status of lymph node metastasis. If, on a conservative assumption, all these three cases had no lymph node metastasis and were included in the analysis, the prevalence of lymph node metastasis in classic PTC would be 43% (instead of 45%) and the p value would be 0.0012 (instead of <0.0001).
+Five cases had no sufficient data to define tumor stage in the classic PTC group.

BRAF Mutation is Inherently Associated with a Poor Prognosis of PTC

Figure 2:
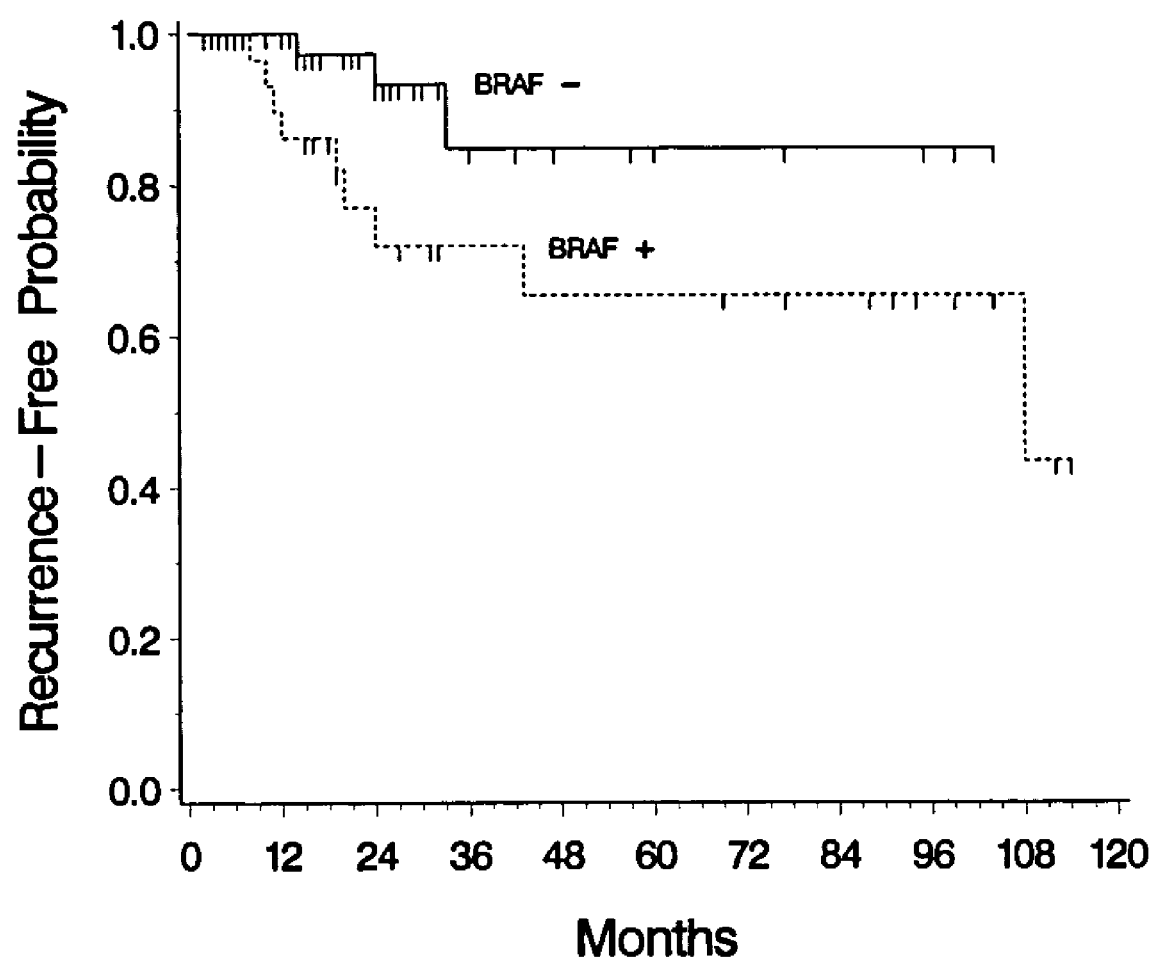
FIG. 2. Kaplan-Meier estimate of cancer recurrence-free probability in BRAF mutation-positive and -negative papillary thyroid cancers. Short vertical lines indicate censored observations (months of follow-up for those that have not had a recurrence). Log-rank chi-square=4.28, p=0.039.

As patient age and gender, and tumor size and multifocality may all potentially affect the clinical outcome and prognosis of thyroid cancer (18); (15), (17); (24) we next performed a multivariate analysis with the adjustment for these factors on the correlation between the BRAF mutation status and each of the high-risk pathologic features (i.e., tumor extrathyroidal invasion, neck lymph node metastasis, and advanced tumor stages) and tumor recurrence. For tumor recurrence, an adjustment for radioiodine treatment was also made since such treatment may alter the clinical outcome of the cancer. As shown in Table 4, with such a multivariate analysis, a significant association (high odd ratio) of BRAF mutation with each of the high-risk pathologic features and tumor recurrence was still observed. Kaplan-Meier estimate revealed a significantly lower tumor recurrence-free probability in PTC patients with BRAF mutation (FIG. 2). Cox proportional hazards regression analysis on tumor recurrence, adjusting for age at diagnosis, gender, tumor size and multifocality, and total dose of I-131 resulted in a statistically significant relative risk of 37.68 (95% CI=1.17-1217.22, p=0.041) for tumor recurrence associated with BRAF mutation. These results suggest that BRAF mutation plays an important role in the tumorigenesis of PTC and inherently predicts a poor prognosis for these cancers.

TABLE 4

Multivariate analysis on adjusted odds ratios for the association of BRAF mutation with clinicopathologic outcomes of patients with papillary thyroid cancer

| | BRAF Mutation | | |
|---|---|---|---|
| | Odds Ratio | 95% Confidence Interval | P value |
| Tumor Stage III/IV* | 3.59 | 1.14-11.34 | 0.029 |
| Lymph Node Metastasis* | 7.74 | 2.81-21.35 | <.0001 |
| Extrathyroidal Invasion* | 8.00 | 2.80-22.85 | 0.0001 |
| Tumor Recurrence+ | 35.80 | 2.02-633.47 | 0.015 |

*Adjusted for age at diagnosis, gender, multifocality, and tumor size
+Also adjusted for total I-131 treatment

REFERENCES (1) Peyssonnaux C, Eychene A. The Raf/MEK/ERK pathway: new concepts of activation. Biol Cell 2001;93:53-62.

(2) Duesbery N S, Webb C P, Vande Woude G F. MEK wars, a new front in the battle against cancer. Nat Med 1999; 5:736-7.

(3) Avruch J, Khokhlatchev A, Kyriakis J M, Luo Z, Tzivion G, Vavvas D, et al. Ras activation of the Raf kinase: tyrosine kinase recruitment of the MAP kinase cascade. Recent Prog Horm Res 2001;56:127-55.=

(4) Davies H, Bignell G R, Cox C, Stephens P, Edkins S, Clegg S, et al. Mutations of the BRAF gene in human cancer. Nature 2002;417:949-54.

(5) Gimm O. Thyroid cancer. Cancer Lett 2001;163:143-56.
(6) Grieco M, Santoro M, Berlingieri M T, Melillo R M, Donghi R, Bongarzone I, et al. PTC is a novel rearranged form of the ret proto-oncogene and is frequently detected in vivo in human thyroid papillary carcinomas. Cell 1990;60:557-63.
(7) Rajagopalan H, Bardelli A, Lengauer C, Kinzler K W, Vogelstein B, Velculescu V E. Tumorigenesis: RAF/RAS oncogenes and mismatch-repair status. Nature 2002;418: 934.
(8) Singer G, Oldt R III, Cohen Y, Wang B G, Sidransky D, Kurman R J, et al. Mutations in BRAF and KRAS characterize the development of low-grade serous ovarian carcinoma. J Natl Cancer Inst. In press 2003.
(9) Ludwig L, Kessler H, Wagner M, Hoang-Vu C, Dralle H, Adler G, et al. Nuclear factor-kappaB is constitutively active in C-cell carcinoma and required for RET-induced transformation. Cancer Res 2001;61:4526-35.
(10) Saavedra H I, Knauf J A, Shirokawa J M, Wang J, Ouyang B, Elisei R, et al. The RAS oncogene induces genomic instability in thyroid PCCL3 cells via the MAPK pathway. Oncogene 2000;19:3948-54.
(11) Specht M C, Barden C B, Fahey T J 3rd. p44/p42-MAP kinase expression in papillary thyroid carcinomas. Surgery 2001;130:936-40.
(12) Lyons J F, Wilhelm S, Hibner B, Bollag G. Discovery of a novel Raf kinase inhibitor. Endocr Relat Cancer 2001;8:219-25.
(13) Cohen Y, Xing M, Mambo E, Guo Z, Wu G, Trink B, Beller U, Westra W H, Ladenson P W, Sidransky D. BRAF mutation in papillary thyroid carcinoma. J Natl Cancer Inst. 2003 Apr. 16;95(8):625-7.
(14) Cox D R. Regression models and life tables (with discussion). *J R Stat Soc B* 1972; 34: 187-220
(15) Fonseca E, Soares P, Rossi S, Sobrinho-Simoes M. Prognostic factors in thyroid carcinomas. Verh Dtsch Ges Pathol. 1997;81:82-96. Review.
(16) Fukushima T, Suzuki S, Mashiko M, Ohtake T, Endo Y, Takebayashi Y, Sekikawa K, Hagiwara K, Takenoshita S. BRAF mutations in papillary carcinomas of the thyroid. Oncogene. 2003 Sep. 25;22(41):6455-7.
(17) Gilliland F D, Hunt W C, Morris D M, Key C R. Prognostic factors for thyroid carcinoma. A population-based study of 15,698 cases from the Surveillance, Epidemiology and End Results (SEER) program 1973-1991. Cancer. 1997 Feb. 1;79(3):564-73.
(18) Hay I D, Bergstralh E J, Goellner J R, Ebersold J R, Grant C S. Predicting outcome in papillary thyroid carcinoma: development of a reliable prognostic scoring system in a cohort of 1779 patients surgically treated at one institution during 1940 through 1989. Surgery. 1993 December;114(6):1050-7; discussion 1057-8.
(19) Hilger R A, Scheulen M E, Strumberg D. The Ras-Raf-MEK-ERK pathway in the treatment of cancer. Onkologie. 2002 December;25(6):511-8.
(20) Hundahl S A, Fleming I D, Fremgen A M, Menck H R. A National Cancer Data Base report on 53,856 cases of thyroid carcinoma treated in the U.S., 1985-1995. Cancer. 1998 Dec. 15;83(12):2638-48.
(21) Kalbfleisch J D, Prentice R L. *The Statistical Analysis of Failure Time Data*. New York: John Wiley & Sons, 1980
(22) Kaplan E L, Meier P. Nonparametric estimation from incomplete observations. *J Am Stat Assoc* 1958; 53: 457-481.
(23) Kimura E T, Nikiforova M N, Zhu Z, Knauf J A, Nikiforov Y E, Fagin J A. High prevalence of BRAF mutations in thyroid cancer: genetic evidence for constitutive activation of the RET/PTC-RAS-BRAF signaling pathway in papillary thyroid carcinoma. Cancer Res. 2003 Apr. 1;63(7):1454-7.
(24) LiVolsi V A, Fadda G, Baloch Z W. Prognostic factors in well-differentiated thyroid cancer. Rays. 2000 April-June;25(2): 163-75.
(25) Mercer K E, Pritchard C A. Raf proteins and cancer: B-Raf is identified as a mutational target. Biochim Biophys Acta. 2003 Jun. 5;1653(1):25-40
(26) Namba H, Nakashima M, Hayashi T, Hayashida N, Maeda S, Rogounovitch T I, Ohtsuru A, Saenko V A, Kanematsu T, Yamashita S. Clinical implication of hot spot BRAF mutation, V599E, in papillary thyroid cancers. J Clin Endocrinol Metab. 2003 September;88(9): 4393-7.
(27) Nikiforova M N, Kimura E T, Gandhi M, Biddinger P W, Knauf J A, Basolo F, Zhu Z, Giannini R, Salvatore G, Fusco A, Santoro M, Fagin J A, Nikiforov Y E. BRAF mutations in thyroid tumors are restricted to papillary carcinomas and anaplastic or poorly differentiated carcinomas arising from papillary carcinomas. J Clin Endocrinol Metab. 2003 November;88(11):5399-404.
(28) Soares P, Trovisco V, Rocha A S, Lima J, Castro P, Preto A, Maximo V, Botelho T, Seruca R, Sobrinho-Simoes M. BRAF mutations and RET/PTC rearrangements are alternative events in the etiopathogenesis of PTC. Oncogene. 2003 Jul. 17;22(29):4578-80.
(29) Xing, M, Vasko V, Tallini G, Larin A, Wu G, Udelsman R, Ringel M D, Ladenson P W, and Sidransky D. BRAF T1796A Transversion Mutation in Various Thyroid Neoplasms. J Clin Endocrinol Metab (in press), 2004a
(30) Xing, M, Tufano, R P, Tufaro, A P, Basaria, S S, Ewertz, M, Byrne, P J, Wang, J, Sidransky, D, and Ladenson, P W. Detection of BRAF mutation on fine needle aspiration biopsy specimens: a new diagnostic tool for papillary thyroid cancer. J Clin Endocrinol Metab (in revision), 2004b
(31) Xing, M, Usadel H, Cohen Y, Tokumaru Y, Guo Z, Westra W B, Tong B C, Tallini G, Udelsman R, Califano J A, Ladenson P W, Sidransky D. Methylation of the thyroid-stimulating hormone receptor gene in epithelial thyroid tumors: a marker of malignancy and a cause of gene silencing. Cancer Res. 2003 (c) May 1;63(9):2316-21.
(32) Xu X, Quiros R M, Gattuso P, Ain K B, Prinz R A 2003 High prevalence of BRAF gene mutation in papillary thyroid carcinomas and thyroid tumor cell lines. Cancer Res 63:4561
(33) Yamashita H, Noguchi S, Murakami N, et al. Extracapsular invasion of lymph node metastasis. A good indicator of disease recurrence and poor prognosis in patients with thyroid microcarcinoma. Cancer. 1999; 86: 842-849.

We claim:

1. A method for distinguishing malignant papillary from benign thyroid samples, comprising:
   determining presence of a T→A transversion at nucleotide 1796 of BRAF according to SEQ ID NO: 1 in a thyroid sample of a human, wherein presence of the transversion indicates a malignant papillary neoplasm and absence of the transversion indicates a benign neoplasm or sample.

2. The method of claim 1 wherein the thyroid sample is a fine needle aspirate (FNA).

3. The method of claim 1 wherein the thyroid sample is a tissue sample.

4. The method of claim 1 wherein the thyroid sample is a cytological sample.

5. The method of claim 1 further comprising:
   providing a diagnosis based on the presence or absence of the transversion.

6. The method of claim 1 further comprising:
   providing a prognosis based on the presence or absence of the transversion.

7. The method of claim 6 wherein if the human has the transversion the prognosis indicates that the human has a higher risk of neck lymph node metastasis than a human without the transversion, and if the human does not have the transversion the prognosis indicates that the human has a lower risk of neck lymph node metastasis than a human with the transversion.

8. The method of claim 6 wherein if the human has the transversion the prognosis indicates that the human has a higher risk of cancer recurrence than a human without the transversion, and if the human does not have the transversion the prognosis indicates that the human has lower risk of cancer recurrence than a human with the transversion.

9. The method of claim 1 further comprising:
   determining a therapeutic regimen for the human using as a factor the presence or absence of the transversion.

10. The method of claim 3 wherein the sample has a follicular morphology.

11. The method of claim 3 wherein the sample as a papillary morphology.

12. A method of detecting a malignant papillary thyroid neoplasm in a human suspected of having a thyroid neoplasm, comprising:
    determining presence of a T→A transversion at nucleotide 1796 of BRAF according to SEQ ID NO: 1 in a blood sample of a human suspected of having a thyroid neoplasm, wherein presence of the transversion indicates a malignant papillary thyroid neoplasm in the human and absence of the transversion indicates a benign thyroid neoplasm or no neoplasm.

13. A method for detecting a T→A transversion mutation at nucleotide 1796 of BRAF according to SEQ ID NO: 1, comprising:
   amplifying all or part of exon 15 of BRAF from a thyroid test sample to form amplified products, wherein said part comprises at least nucleotides 1792 to 1799 of BRAF;
   digesting the amplified products with restriction endonuclease TspRI to form digested products;
   identifying a mutation at nucleotide 1796 if the digested products contain:
      one fragment fewer than digested products formed when using wild-type BRAF as a template for amplifying and digesting; or
      one additional fragment compared to digested products formed when using wild-type BRAF as a template for amplifying or digesting.

14. The method of claim 13 wherein the test sample is an FNA from a thyroid.

15. The method of claim 13 wherein the test sample is a tissue sample from a thyroid.

* * * * *

SEQUENCE LISTING

<160> NUMBER OF SEQ ID NOS: 5

<210> SEQ ID NO 1
<211> LENGTH: 2513
<212> TYPE: DNA
<213> ORGANISM: Homo sapiens

<400> SEQUENCE: 1

| | | | | | |
|---|---|---|---|---|---|
| cgcctcccgg | cccctcccc | gcccgacagc | ggccgctcgg | gccccggctc | tcggttataa | 60 |
| gatggcggcg | ctgagcggtg | gcggtggtgg | cggcgcggag | ccgggccagg | ctctgttcaa | 120 |
| cggggacatg | gagcccgagg | ccggcgccgg | cgccggcgcc | gcggcctctt | cggctgcgga | 180 |
| ccctgccatt | ccgaggagg | tgtggaatat | caaacaaatg | attaagttga | cacaggaaca | 240 |
| tatagaggcc | ctattggaca | aatttggtgg | ggagcataat | ccaccatcaa | tatatctgga | 300 |
| ggcctatgaa | gaatacacca | gcaagctaga | tgcactccaa | caaagagaac | aacagttatt | 360 |
| ggaatctctg | gggaacggaa | ctgattttc | tgtttctagc | tctgcatcaa | tggataccgt | 420 |
| tacatcttct | tcctcttcta | gcctttcagt | gctaccttca | tctctttcag | ttttcaaaa | 480 |
| tcccacagat | gtggcacgga | gcaaccccaa | gtcaccacaa | aaacctatcg | ttagagtctt | 540 |
| cctgcccaac | aaacagagga | cagtggtacc | tgcaaggtgt | ggagttacag | tccgagacag | 600 |
| tctaaagaaa | gcactgatga | tgagaggtct | aatcccagag | tgctgtgctg | tttacagaat | 660 |
| tcaggatgga | gagaagaaac | caattggttg | ggacactgat | atttcctggc | ttactggaga | 720 |
| agaattgcat | gtggaagtgt | tggagaatgt | tccacttaca | acacacaact | tgtacgaaa | 780 |
| aacgttttc | accttagcat | tttgtgactt | ttgtcgaaag | ctgcttttcc | agggtttccg | 840 |
| ctgtcaaaca | tgtggttata | aatttcacca | gcgttgtagt | acagaagttc | cactgatgtg | 900 |
| tgttaattat | gaccaacttg | atttgctgtt | tgtctccaag | ttctttgaac | cacccaat | 960 |
| accacaggaa | gaggcgtcct | tagcagagac | tgccctaaca | tctggatcat | cccttccgc | 1020 |
| acccgcctcg | gactctattg | gccccaaat | tctcaccagt | ccgtctcctt | caaaatccat | 1080 |
| tccaattcca | cagcccttcc | gaccagcaga | tgaagatcat | cgaaatcaat | tgggcaacg | 1140 |
| agaccgatcc | tcatcagctc | ccaatgtgca | tataaacaca | atagaacctg | tcaatattga | 1200 |
| tgacttgatt | agagaccaag | gatttcgtgg | tgatggagga | tcaaccacag | gtttgtctgc | 1260 |
| tacccccct | gcctcattac | ctggctcact | aactaacgtg | aaagcccttac | agaaatctcc | 1320 |
| aggacctcag | cgagaaagga | agtcatcttc | atcctcagaa | acaggaatc | gaatgaaaac | 1380 |
| acttggtaga | cgggactcga | gtgatgattg | ggagattcct | gatgggcaga | ttacagtggg | 1440 |
| acaaagaatt | ggatctggat | catttggaac | agtctacaag | ggaaagtggc | atggtgatgt | 1500 |
| ggcagtgaaa | atgttgaatg | tgacagcacc | taccctcag | cagttacaag | ccttcaaaaa | 1560 |
| tgaagtagga | gtactcagga | aaacacgaca | tgtgaatatc | ctactcttca | tgggctattc | 1620 |
| cacaaagcca | caactggcta | ttgttaccca | gtggtgtgag | ggctccagct | tgtatcacca | 1680 |
| tctccatatc | attgagacca | aatttgagat | gatcaaactt | atagatattg | cacgacagac | 1740 |
| tgcacagggc | atggattact | tacacgccaa | gtcaatcatc | cacagagacc | tcaagagtaa | 1800 |
| taatatattt | cttcatgaag | acctcacagt | aaaaataggt | gattttggtc | tagctacagt | 1860 |
| gaaatctcga | tggagtgggt | cccatcagtt | tgaacagttg | tctggatcca | ttttgtggat | 1920 |
| ggcaccagaa | gtcatcagaa | tgcaagataa | aaatccatac | agctttcagt | cagatgtata | 1980 |
| tgcatttgga | attgttctgt | atgaattgat | gactggacag | ttaccttatt | caaacatcaa | 2040 |

```
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa aaaaaaaaaa aaaaaaaaa aaaaaaaaaa ccc            2513
```

<210> SEQ ID NO 2
<211> LENGTH: 23
<212> TYPE: DNA
<213> ORGANISM: Homo sapiens

<400> SEQUENCE: 2
tcataatgct tgctctgata gga                                            23

<210> SEQ ID NO 3
<211> LENGTH: 22
<212> TYPE: DNA
<213> ORGANISM: Homo sapiens

<400> SEQUENCE: 3
ggccaaaaat ttaatcagtg ga                                             22

<210> SEQ ID NO 4
<211> LENGTH: 766
<212> TYPE: PRT
<213> ORGANISM: Homo sapiens

<400> SEQUENCE: 4

Met Ala Ala Leu Ser Gly Gly Gly Gly Gly Ala Glu Pro Gly Gln
  1               5                  10                  15

Ala Leu Phe Asn Gly Asp Met Glu Pro Glu Ala Gly Ala Gly Ala Gly
              20                  25                  30

Ala Ala Ala Ser Ser Ala Ala Asp Pro Ala Ile Pro Glu Glu Val Trp
          35                  40                  45

Asn Ile Lys Gln Met Ile Lys Leu Thr Gln Glu His Ile Glu Ala Leu
 50                  55                  60

Leu Asp Lys Phe Gly Gly Glu His Asn Pro Pro Ser Ile Tyr Leu Glu
 65                  70                  75                  80

Ala Tyr Glu Glu Tyr Thr Ser Lys Leu Asp Ala Leu Gln Gln Arg Glu
                 85                  90                  95

Gln Gln Leu Leu Glu Ser Leu Gly Asn Gly Thr Asp Phe Ser Val Ser
             100                 105                 110

Ser Ser Ala Ser Met Asp Thr Val Thr Ser Ser Ser Ser Ser Ser Leu
         115                 120                 125

Ser Val Leu Pro Ser Ser Leu Ser Val Phe Gln Asn Pro Thr Asp Val
     130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                 165                 170                 175

Val Arg Asp Ser Leu Lys Lys Ala Leu Met Met Arg Gly Leu Ile Pro
             180                 185                 190

-continued

```
Glu Cys Cys Ala Val Tyr Arg Ile Gln Asp Gly Glu Lys Lys Pro Ile
            195                 200                 205
Gly Trp Asp Thr Asp Ile Ser Trp Leu Thr Gly Glu Glu Leu His Val
        210                 215                 220
Glu Val Leu Glu Asn Val Pro Leu Thr Thr His Asn Phe Val Arg Lys
225                 230                 235                 240
Thr Phe Phe Thr Leu Ala Phe Cys Asp Phe Cys Arg Lys Leu Leu Phe
                245                 250                 255
Gln Gly Phe Arg Cys Gln Thr Cys Gly Tyr Lys Phe His Gln Arg Cys
            260                 265                 270
Ser Thr Glu Val Pro Leu Met Cys Val Asn Tyr Asp Gln Leu Asp Leu
        275                 280                 285
Leu Phe Val Ser Lys Phe Phe Glu His His Pro Ile Pro Gln Glu Glu
290                 295                 300
Ala Ser Leu Ala Glu Thr Ala Leu Thr Ser Gly Ser Ser Pro Ser Ala
305                 310                 315                 320
Pro Ala Ser Asp Ser Ile Gly Pro Gln Ile Leu Thr Ser Pro Ser Pro
                325                 330                 335
Ser Lys Ser Ile Pro Ile Pro Gln Pro Phe Arg Pro Ala Asp Glu Asp
            340                 345                 350
His Arg Asn Gln Phe Gly Gln Arg Asp Arg Ser Ser Ala Pro Asn
        355                 360                 365
Val His Ile Asn Thr Ile Glu Pro Val Asn Ile Asp Asp Leu Ile Arg
        370                 375                 380
Asp Gln Gly Phe Arg Gly Asp Gly Gly Ser Thr Thr Gly Leu Ser Ala
385                 390                 395                 400
Thr Pro Pro Ala Ser Leu Pro Gly Ser Leu Thr Asn Val Lys Ala Leu
                405                 410                 415
Gln Lys Ser Pro Gly Pro Gln Arg Glu Arg Lys Ser Ser Ser Ser Ser
            420                 425                 430
Glu Asp Arg Asn Arg Met Lys Thr Leu Gly Arg Arg Asp Ser Ser Asp
        435                 440                 445
Asp Trp Glu Ile Pro Asp Gly Gln Ile Thr Val Gly Gln Arg Ile Gly
        450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
                485                 490                 495
Ala Phe Lys Asn Glu Val Gly Val Leu Arg Lys Thr Arg His Val Asn
            500                 505                 510
Ile Leu Leu Phe Met Gly Tyr Ser Thr Lys Pro Gln Leu Ala Ile Val
        515                 520                 525
Thr Gln Trp Cys Glu Gly Ser Ser Leu Tyr His His Leu His Ile Ile
        530                 535                 540
Glu Thr Lys Phe Glu Met Ile Lys Leu Ile Asp Ile Ala Arg Gln Thr
545                 550                 555                 560
Ala Gln Gly Met Asp Tyr Leu His Ala Lys Ser Ile Ile His Arg Asp
                565                 570                 575
Leu Lys Ser Asn Asn Ile Phe Leu His Glu Asp Leu Thr Val Lys Ile
            580                 585                 590
Gly Asp Phe Gly Leu Ala Thr Val Lys Ser Arg Trp Ser Gly Ser His
        595                 600                 605
```

-continued

```
Gln Phe Glu Gln Leu Ser Gly Ser Ile Leu Trp Met Ala Pro Glu Val
    610                 615                 620
Ile Arg Met Gln Asp Lys Asn Pro Tyr Ser Phe Gln Ser Asp Val Tyr
625                 630                 635                 640
Ala Phe Gly Ile Val Leu Tyr Glu Leu Met Thr Gly Gln Leu Pro Tyr
                645                 650                 655
Ser Asn Ile Asn Asn Arg Asp Gln Ile Ile Phe Met Val Gly Arg Gly
            660                 665                 670
Tyr Leu Ser Pro Asp Leu Ser Lys Val Arg Ser Asn Cys Pro Lys Ala
        675                 680                 685
Met Lys Arg Leu Met Ala Glu Cys Leu Lys Lys Lys Arg Asp Glu Arg
    690                 695                 700
Pro Leu Phe Pro Gln Ile Leu Ala Ser Ile Glu Leu Leu Ala Arg Ser
705                 710                 715                 720
Leu Pro Lys Ile His Arg Ser Ala Ser Glu Pro Ser Leu Asn Arg Ala
                725                 730                 735
Gly Phe Gln Thr Glu Asp Phe Ser Leu Tyr Ala Cys Ala Ser Pro Lys
            740                 745                 750
Thr Pro Ile Gln Ala Gly Gly Tyr Gly Ala Phe Pro Val His
        755                 760                 765

<210> SEQ ID NO 5
<211> LENGTH: 119
<212> TYPE: DNA
<213> ORGANISM: Homo sapiens
<220> FEATURE:
<221> NAME/KEY: exon
<222> LOCATION: (1)...(119)
<223> OTHER INFORMATION: exon 15

<400> SEQUENCE: 5
atatatttct tcatgaagac ctcacagtaa aaataggtga ttttggtcta gctacagtga      60
aatctcgatg gagtgggtcc catcagtttg aacagttgtc tggatccatt ttgtggatg     119
```